United States Patent [19]

Suval

[11] Patent Number: 5,611,358
[45] Date of Patent: Mar. 18, 1997

[54] METHOD AND APPARATUS FOR TREATING VARICOSE VEINS

[76] Inventor: William D. Suval, 15201 Eleventh St. Suite 300, Victorville, Calif. 92392

[21] Appl. No.: 525,843

[22] Filed: Sep. 8, 1995

[51] Int. Cl.⁶ .......................... A61B 19/00; A61B 17/08
[52] U.S. Cl. ............................ 128/898; 606/158
[58] Field of Search .................... 128/898; 606/158, 606/159, 144, 148

[56]       References Cited

U.S. PATENT DOCUMENTS

| | | | |
|---|---|---|---|
| 3,954,108 | 5/1976 | Davis | 606/158 X |
| 4,058,126 | 11/1977 | Leveen | 606/158 X |
| 4,760,846 | 8/1988 | Mers Kelly et al. | 606/158 X |
| 4,827,929 | 5/1989 | Hodge | 606/158 X |
| 4,877,028 | 10/1989 | Sanhaus | 606/158 |
| 4,881,939 | 11/1989 | Newman | 606/158 X |
| 5,254,095 | 10/1993 | Harvey | 606/158 X |
| 5,282,812 | 2/1994 | Suarez et al. | 606/158 |
| 5,304,183 | 4/1994 | Gourlay et al. | 606/41 |
| 5,306,283 | 4/1994 | Conners | 606/158 X |
| 5,366,458 | 11/1994 | Korthoff et al. | 606/157 |

*Primary Examiner*—Michael Powell Buiz
*Assistant Examiner*—Nancy Connolly Mulcare
*Attorney, Agent, or Firm*—Graham & James LLP

[57]            ABSTRACT

A minimally invasive percutaneous ligation method for treating a varicose vein is provided. The junction between the varicose vein and the deep veins of the patient's leg are first ligated by conventional techniques. Then, a sterile closure is pierced through a skin layer adjacent to a varicose region of the vein such that at least a portion of the sterile closure remains external to the skin layer. The varicose vein is at least partially obstructed with the sterile closure to promote intentional scarring of the vein. Finally, the sterile closure is removed back through the skin layer after a sufficient amount of scarring of the vein has occurred. The sterile closure may comprise a surgical staple, a pin or a screw.

6 Claims, 3 Drawing Sheets

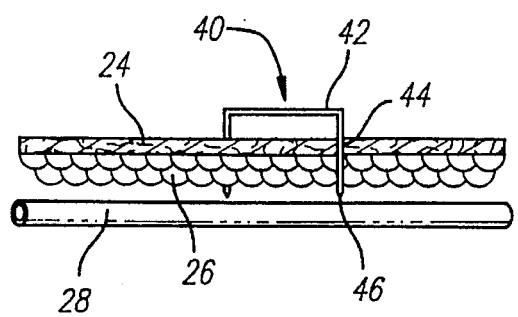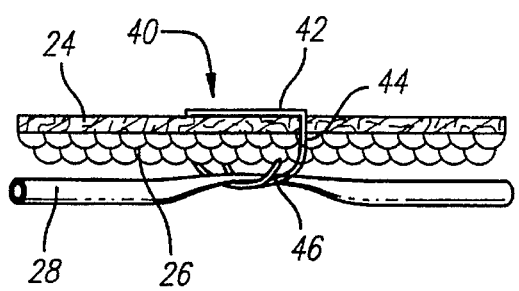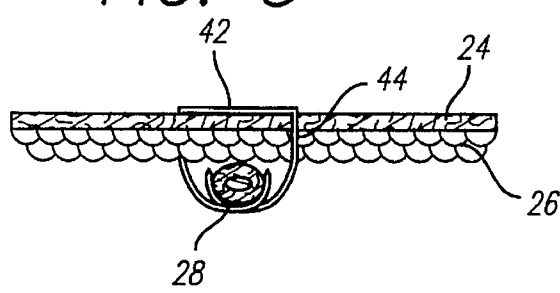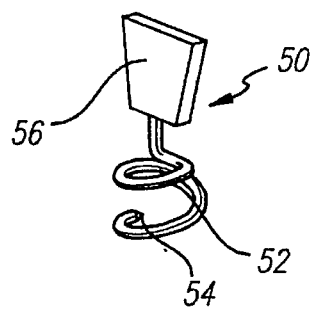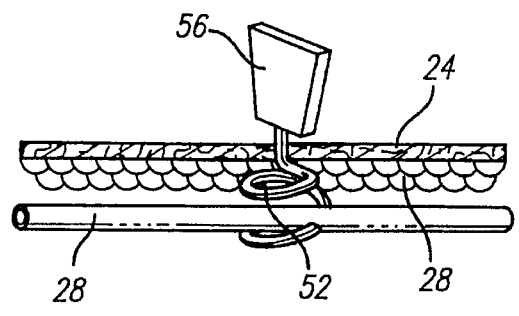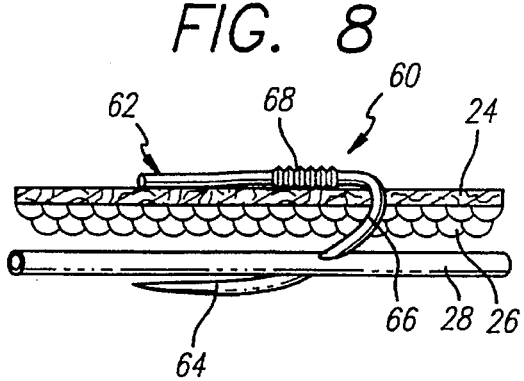

5,611,358

METHOD AND APPARATUS FOR TREATING VARICOSE VEINS

RELATED APPLICATION

This application relates to co-pending application Ser. No. 08/385,794 for METHOD AND APPARATUS FOR TREATING VARICOSE VEINS.

BACKGROUND OF THE INVENTION

1. Field of the Invention

The present invention relates to medical treatment of varicose veins, and more particularly, to a minimally invasive method and apparatus for treating varicose veins that allows for complete obliteration of the affected veins without scarring or any of the other undesirable complications of conventional treatments.

2. Description of Related Art

Varicose veins is a medical condition present in up to twenty-five percent of the adult population, and is especially prevalent among middle-aged women. The term "varicose" is derived from the Greek word for "grape-like" and refers to the torturous appearance of the afflicted veins. Patients suffering from varicose veins often experience various symptoms, including aching, itching, heaviness, swelling or cramping of the legs, while more serious complications of varicose veins can include thrombophlebitis, dermatitis, hemorrhage and ulcers. Even absent such complications, many patients seek medical treatment of varicose veins for primarily cosmetic reasons due to the generally unsightly appearance that characterizes the condition.

Specifically, varicose veins are a condition of the superficial veins of the legs in which the veins have become abnormally twisted, lengthened, or dilated. The condition is usually caused by inefficient or defective one-way valves within the veins. These one-way valves provide an important function in controlling blood pressure within the venous system of the legs. During walking, the leg muscles provide a musculovenous pump that compresses the veins and propels blood to the heart. Efficiency of the musculovenous pump is enhanced by the one-way valves within the veins that protect the venous system at the lower extremities from excess pressure generated by coughing, straining, lifting, standing or other such exertion. The superficial veins normally carry only ten to fifteen percent of the blood, with the remainder carried by the deep veins; however, the percentage of blood carried by the superficial veins can exceed these normal levels due to dilation of the superficial veins or thrombosis of the deep veins. As a result, the one-way valves can become incompetent which further increases retrograde pressure within the superficial veins. Since the superficial veins lie close to the skin layer and are poorly supported by the subcutaneous tissue, the increased retrograde pressure causes the varicose veins to be formed.

There are two known types of treatment for varicose veins. A first type of treatment comprises surgical removal of the superficial varicose veins, also referred to as "vein stripping." In the stripping technique, a surgeon first makes an incision at the groin area through which the saphenous vein is separated from the femoral vein. The saphenous vein is also dissected at the foot, and at that point, a vein stripper, such as a wire, is inserted into the lumen of the saphenous vein. The wire is then threaded through the saphenous vein to the incision at the groin. The wire includes a nut at an end thereof that catches on the foot end of the saphenous vein. The surgeon then removes the wire though the groin incision to gently extract the vein. It is further necessary to make multiple small incisions along the leg in order to disconnect the numerous tributary veins from the saphenous vein and to ligate these tributary veins. Once the saphenous vein is completely removed from the leg, the various incision wounds can be sutured closed.

The stripping technique represents a permanent solution in that the varicose vein condition cannot recur once the vein has been removed. Nevertheless, the technique has numerous significant drawbacks that render it an unsatisfactory treatment. The numerous incisions often leave substantial unsightly scars along the legs that can be as unpleasant in appearance as the original varicose vein condition. Moreover, the procedure is generally performed under general anesthesia and often requires an overnight hospital stay. There are also associated complications of the technique, such as blood loss, pain, infection, hematoma, nerve injury and swelling. After undergoing the stripping technique, a patient generally requires several weeks to recover. In view of these significant drawbacks, the stripping technique is recommended only for extreme cases of varicose veins, and for patients that are in sufficiently good health to handle the surgery.

A second technique for treating varicose veins is known as sclerotherapy. This technique involves injection of toxic fluids, such as sodium tetradecyl sulfate, into the veins to cause subsequent inflammation and sclerosis of the veins. The sclerosis results in localized scarring or closure of the veins, which forces rerouting of the blood away from the affected veins. The sclerotherapy technique is often combined with an operative procedure, such as ligation of a portion of the saphenous vein.

While the sclerotherapy technique is less surgically intensive than the stripping technique, it often does not represent a permanent or complete solution since it has a high rate of recurrence and cannot be applied to the saphenous vein in the upper thigh region due to the risk of sclerosis of the deep veins. Sclerotherapy has other potentially serious complications, including skin staining, ulceration, phlebitis, allergic or anaphylactic overdose, ischemia, skin or fat necrosis, and peripheral neuropathy. Notwithstanding these complications, patients must often undergo multiple courses of sclerotherapy treatment in order to completely alleviate the varicose veins to a satisfactory degree.

In view of these significant drawbacks of the conventional treatments for varicose veins, a critical need exists for a minimally invasive and permanent treatment for varicose veins. Such a treatment should provide for complete obliteration of the affected veins without visible scarring, excess hospitalization or any of the other undesirable complications of the conventional treatments.

SUMMARY OF THE INVENTION

In accordance with the teachings of the present invention, a minimally invasive method for treating a varicose vein is provided. The method provides for complete obliteration of the affected veins without visible scarring, hospitalization or any of the other undesirable complications of the conventional treatments.

Generally, the method comprises four steps: (a) ligating the junction between the varicose vein and the deep veins of the patient's leg; (b) piercing through a skin layer adjacent to a varicose region of the vein with a sterile closure such that at least a portion of the sterile closure remains external to the skin layer; (c) at least partially obstructing the varicose vein with the sterile closure to promote intentional scarring of the vein; and (d) removing the closure back through the skin layer after a sufficient amount of scarring of the vein has occurred.

More specifically, the vein is at least partially obstructed by either impaling the vein or compressing the vein with the sterile closure. In a first embodiment, the sterile closure further comprises a surgical staple and the piercing step further comprises injecting the staple through the skin layer. In another embodiment, the sterile closure further comprises a screw and the piercing step further comprises threading the screw through the skin layer. In yet another embodiment, the sterile closure comprises a pin and the piercing step further comprises piercing the pin through the skin layer.

A more complete understanding of the method and apparatus for treating varicose veins will be afforded to those skilled in the art, as well as a realization of additional advantages and objects thereof, by a consideration of the following detailed description of the preferred embodiment. Reference will be made to the appended sheets of drawings which will first be described briefly.

BRIEF DESCRIPTION OF THE DRAWINGS

FIGS. 3 through 5 illustrate cross-sectional views of a skin layer and superficial vein with a first embodiment of the present invention for obstructing the superficial vein;

FIG. 6 illustrates an apparatus for obstructing the superficial vein according to a second embodiment of the present invention;

FIG. 7 is a cross-sectional view of the skin layer and the superficial vein obstructed with the apparatus of FIG. 6; and FIG. 8 is a cross-sectional view of the skin layer and the superficial vein obstructed according to a third embodiment of the present invention.

DETAILED DESCRIPTION OF THE PREFERRED EMBODIMENT

Figure 1:
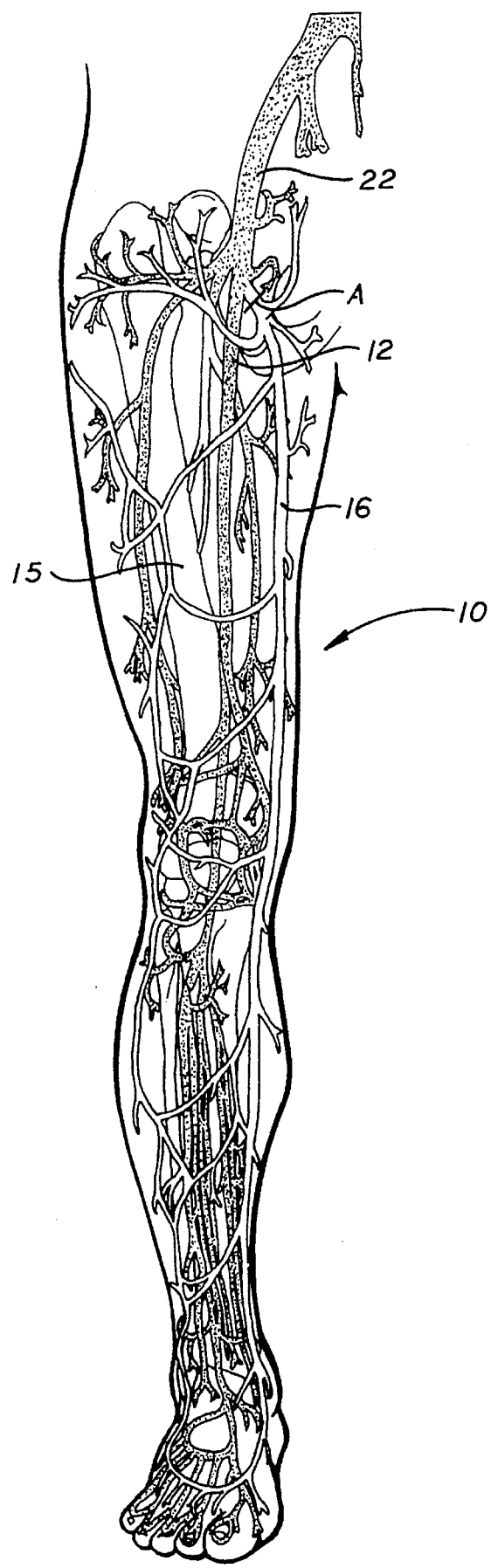
FIG. 1 illustrates a leg showing the superficial and deep venous systems.

The present invention overcomes the significant drawbacks of the conventional treatments for varicose veins, and satisfies the critical need for a minimally invasive and permanent treatment for varicose veins. The treatment of the present invention provides for complete obliteration of the affected veins without visible scarring, hospitalization or any of the other undesirable complications of the conventional treatments. In the detailed description that follows, like reference numerals are used to identify like elements in one or more of the figures.

Referring first to FIG. 1, the venous system of a leg 10 is illustrated. The venous system includes the deep veins 12 that lie close to the leg bones 15 and carry a majority of the blood, and the superficial veins 14 that lie close to the skin. The superficial veins 14 include the saphenous vein 16 and a plurality of tributary veins 18. As known in the art, these superficial veins 14 are most susceptible to the varicose vein condition since they are not well supported by muscle and are most visible due to their proximity to the skin.

A first step in treating varicose veins is to disconnect the saphenous vein 16 at its juncture with the femoral vein 22 (greater saphenous-femoral junction). This way, additional blood from the deep veins 12 will be prevented from backing into the saphenous vein 16, eliminating the primary cause of the varicose veins. While blood can still enter the saphenous vein 16 through the numerous tributary veins 18, the subsequent permanent closure of the saphenous vein (described below) will effectively prevent this occurrence. As in the prior art stripping technique, an incision in the groin area is necessary to disconnect the saphenous vein 16 (incision indicated as line segment A of FIG. 1). The saphenous vein 16 is located directly beneath a deep layer of the superficial fascia, and is normally ligated flush with the femoral vein 22. As will be understood from the description that follows, this groin incision will be the only one that requires suturing for closure and that may leave a scar; however, the proximity of the incision to the inguinal skin fold means that any incision scar will not be visible as a practical matter.

Alternatively, the saphenous vein 16 can be disconnected from the deep veins at a lower point along the leg, such as behind the knee at the lesser saphenous-popliteal junction. This alternative technique may be advisable in circumstances in which treatment of varicose veins is only necessary in the lower leg.

Figure 2:
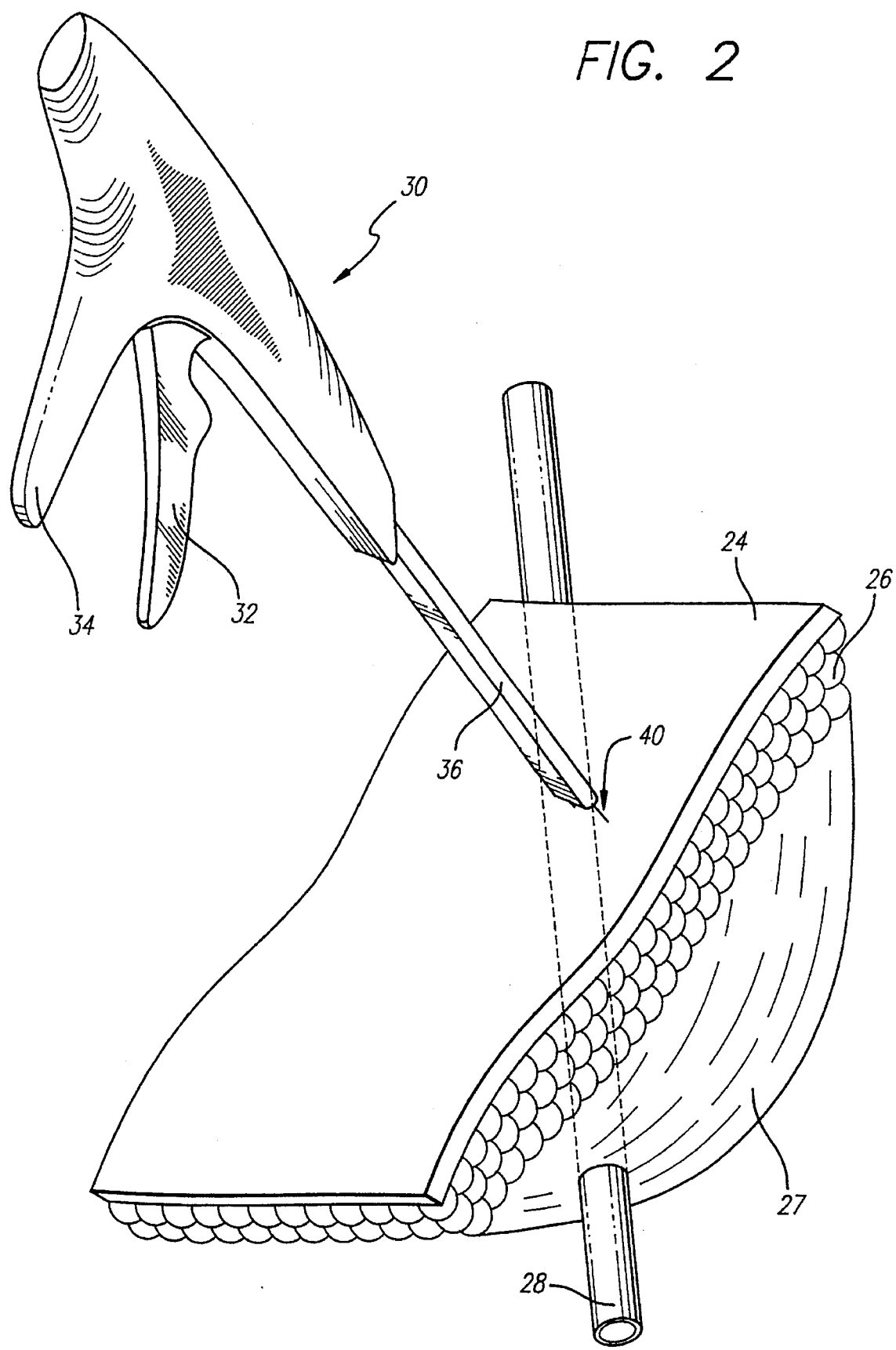
FIG. 2 is a partial perspective view of a portion of the leg showing the skin layer and a superficial vein.

Once the saphenous vein 16 is disconnected from the femoral vein 22, the varicose veins can be treated in accordance with the method of the present invention. Referring now to FIG. 2, a partial perspective view of a portion of the leg showing the skin layer 24, subcutaneous tissue 26 and a segment of a superficial vein 28 is illustrated. The superficial vein 28 lies between layers of subcutaneous tissue 26 and sartorius muscle 27. The specific segment of superficial vein 28 requiring treatment may comprise the saphenous vein 16 or one of the tributary veins 18, depending on the specific condition of the particular patient.

In accordance with the method of the present application, a sterile closure device is introduced through the skin layer 24 to obstruct, compress or otherwise obliterate a portion of the superficial vein 28, a procedure referred to herein as a percutaneous ligation. The sterile closure device will remain in place with a portion extending outwardly through the skin layer 24 for period of time until the vein 28 has scarred closed. Subsequently, the sterile closure can be removed from the skin layer 25 and vein 28, to allow the skin to heal. By using a non-reactive material for the sterile closure, and by keeping the size of the closure relatively small, any scarring of the skin will be minimized. Moreover, the procedure can be performed on an outpatient basis without any of the usual complications of conventional surgical procedures.

FIGS. 2 through 5 illustrates a first embodiment the present method, which utilizes a conventional surgical stapler type device. As known in the art, surgical staplers are used to suture skin and other fascia together. In this method, the stapler is used to close the vein 28 in a minimally invasive manner. In FIG. 2, the surgical stapler 30 is brought into proximity with the skin to perform the percutaneous ligation procedure. The conventional surgical stapler 30 comprises a handle portion 34, a trigger 32, and a cartridge 36. The cartridge 36 holds a supply of staples, and has a dispensing region at a distal end thereof. Upon application of pressure on the trigger 32 by drawing it close to the handle portion 34, a single staple 40 is dispensed from the distal end of the cartridge 36.

For convenience of illustration, the stapler 30 is not shown in FIGS. 3 through 5, but it should be apparent that the stapler will remain in substantially the same position as shown in FIG. 2. As illustrated in FIG. 3, the staple 40 includes a bridge 42 and a pair of prongs 44 disposed perpendicularly to the bridge. Each of the prongs 44 has a sharpened tip 46 that can readily and cleanly protrude through the skin layer 24. The staple 40 may be comprised of non-reactive material, such as stainless steel, that would preclude infection of the skin. In FIG. 3, the staple is introduced through the skin layer 24 and subcutaneous tissue 26 so that the prongs 44 straddle either side of the vein 28. Then, in FIG. 4, as pressure continues to be applied by the operation of the stapler, the prongs 44 begin to close around the vein 28 and draw it toward the skin layer 24. In FIG. 5, the vein 28 has almost completely compressed by operation of the staple 40. In the alternative, the staple 40 may be inserted so that one or both of the prongs 44 puncture at least partially through the vein 28.

As known in the art, even a partial obstruction of the vein 28 has the effect of permanently closing the vein. The patient's natural inflammation-repair response system will cause the vein to scar at the internal portion of the vein in the region of the puncture or compression, thus all blood flow through the vein will cease. Eventually, the pigmentation and swelling associated with the varicose vein condition will disappear. After a few days, the vein 28 will have closed, and the staple 40 is removed using a conventional removing tool. Thereafter, the remaining wound of the skin can be treated and closed, such as by sterile tape. As noted previously, the sharpness of the prongs 44 coupled with the narrow gauge of the staple 40 will produce a relatively insignificant wound that should close without any noticeable scarring.

FIGS. 6 and 7 illustrate an alternative embodiment of the present invention, in which a screw-like device is threaded through the skin layer into the varicose vein. In FIG. 6, a screw device 50 comprises a coiled portion 52 having a sharpened end 54. A grasping member 56 is provided at an end opposite from the sharpened end 54. FIG. 7 illustrates the screw device 50 threaded through a skin layer 24 so that the sharpened end 54 impales the vein 28. To thread the screw device 50 through the skin layer, the grasping member 56 is rotated by the surgeon either manually or by use of a rotatable tool. As with the surgical staple described above, the partial obstruction of the vein 28 will cause it to close. Thereafter, the screw device 50 is removed and the skin wound is treated and closed.

Like the surgical staple, the screw device 50 is comprised of a non-reactive, small gauge material, such as stainless steel wire. The grasping member 56 may have a substantially flat surface that lies perpendicular to the skin surface, as illustrated in FIGS. 6 and 7, for ease of manual insertion. Alternatively, the grasping member 56 may be disposed parallel to the skin surface so that it does not protrude outwardly. Such a configuration may be more easily concealed by the patient under sterile tapes or bandages until the device is removed. The grasping member 56 may further include an indentation or other surface feature that can be engaged by a rotatable tool, such as screwdriver slot or Allen socket.

FIG. 8 illustrates another alternative embodiment of the present invention in which a pin is pierced through the skin layer into the varicose vein. The pin 60 is substantially U-shaped, with a pointed end 64, a dull end 62, a gripping portion 68, and a bend 66. The pin 60 can be drawn along the skin surface so that the pointed end 64 pierces the skin and impales the vein 28. The bend 66 catches on the skin and prevents the pin 60 from going too deep into the skin. The gripping portion 68 comprises waves or undulations in the dull end 62 that keep the pin from changing position after insertion. The dull end 62 lies flat against the skin surface and can be covered with sterile tape or bandages. Like the other sterile closure devices described above, the pin device 60 is comprised of a non-reactive, small gauge material, such as stainless steel wire.

Having thus described a preferred embodiment of a method and apparatus for treating varicose veins, it should be apparent to those skilled in the art that certain advantages of the within system have been achieved. It should also be appreciated that various modifications, adaptations, and alternative embodiments thereof may be made within the scope and spirit of the present invention. The invention is further defined by the following claims.

What is claimed is:

1. A minimally invasive method for treating a varicose vein, comprising the steps of:

ligating the junction between said vein and deep veins of the patient's leg;

piercing through a skin layer adjacent to a varicose region of said vein with a sterile closure such that at least a portion of said sterile closure remains external to the skin layer;

at least partially obstructing said vein with said sterile closure to promote scarring of said vein; and removing said sterile closure after a sufficient amount of scarring of said vein has occurred, such that said vein is permanently closed.

2. The method of claim 1, wherein said at least partially obstructing step further comprises impaling said vein with said sterile closure.

3. The method of claim 1, wherein said at least partially obstructing step further comprises compressing said vein with said sterile closure.

4. The method of claim 1, wherein said sterile closure further comprises a surgical staple and said piercing step further comprises injecting said staple through said skin layer.

5. The method of claim 1, wherein said sterile closure further comprises a screw and said piercing step further comprises threading said screw through said skin layer.

6. The method of claim 1, wherein said sterile closure further comprises a pin and said piercing step further comprises piercing said pin through said skin layer.

* * * * *